(12) United States Patent
Zamora et al.

(10) Patent No.: US 6,685,912 B2
(45) Date of Patent: *Feb. 3, 2004

(54) POST-LABELING STABILIZATION OF RADIOLABELED PROTEINS AND PEPTIDES

(75) Inventors: Paul O. Zamora, Gaithersberg, MD (US); Michael J. Marek, Albuquerque, NM (US)

(73) Assignee: Rhomed Incorporated, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/136,666

(22) Filed: Apr. 30, 2002

(65) Prior Publication Data

US 2003/0017108 A1 Jan. 23, 2003

Related U.S. Application Data

(63) Continuation of application No. 09/900,390, filed on Jul. 6, 2001, now abandoned, which is a continuation of application No. 09/393,581, filed on Sep. 9, 1999, now Pat. No. 6,261,536, which is a continuation of application No. 08/794,311, filed on Feb. 3, 1997, now Pat. No. 6,066,309, which is a continuation-in-part of application No. 08/794,270, filed on Jan. 31, 1997, now abandoned.

(60) Provisional application No. 60/011,027, filed on Feb. 2, 1996.

(51) Int. Cl.⁷ ........................ A61K 51/00; A61M 36/14
(52) U.S. Cl. .................... 424/1.49; 424/1.11; 424/1.65; 424/9.1; 424/179.1
(58) Field of Search .............................. 424/1.11, 1.65, 424/1.69, 1.53, 9.1, 804–805, 806, 807; 530/300, 311, 317, 333, 334, 338, 863, 864, 350, 866, 861, 862

(56) References Cited

U.S. PATENT DOCUMENTS

| | | | |
|---|---|---|---|
| 4,401,646 A | 8/1983 | Rhodes et al. | 424/1 |
| 4,510,125 A | 4/1985 | Grogg et al. | 424/1.1 |
| 4,707,353 A | 11/1987 | Bugaj et al. | 424/1.1 |
| 4,988,496 A | 1/1991 | Srinivasan et al. | 424/1.1 |
| 5,078,985 A | 1/1992 | Rhodes | 424/1.1 |
| 5,102,990 A | 4/1992 | Rhodes | 530/391.5 |
| 5,219,556 A | 6/1993 | Wolfangel | 424/1.1 |
| 5,250,666 A | 10/1993 | Gustavson et al. | 530/391.5 |
| 5,277,892 A | 1/1994 | Rhodes | 424/1.69 |
| 5,308,603 A | 5/1994 | Thakur | 424/1.49 |
| 5,384,113 A | 1/1995 | Deutsch et al. | 424/1.69 |
| 5,393,512 A | 2/1995 | Vanderheyden et al. | 424/1.53 |
| 5,443,816 A | 8/1995 | Zamora et al. | 424/1.169 |
| 5,460,785 A | 10/1995 | Rhodes et al. | 424/1.49 |
| 5,679,318 A | 10/1997 | Vanderheyden et al. | 424/1.11 |
| 5,700,444 A | 12/1997 | Zamora et al. | 424/1.69 |
| 5,759,515 A | 6/1998 | Rhodes | 424/1.69 |
| 6,066,309 A | 5/2000 | Zamora et al. | 424/1.49 |
| 6,261,536 B1 * | 7/2001 | Zamora et al. | 424/1.49 |
| 2001/0055563 A1 * | 12/2001 | Zamora et al. | 424/1.69 |

* cited by examiner

*Primary Examiner*—Dameron L. Jones
(74) *Attorney, Agent, or Firm*—Darby & Darby

(57) ABSTRACT

The subject invention relates to the use of ascorbic acid and derivatives thereof in stabilizing radiolabeled proteins and peptides against oxidation loss of radiolabel and autoradiolysis. Ascorbic acid is added after radiolabeling, including any required incubation period, but prior to patient administration.

6 Claims, 13 Drawing Sheets

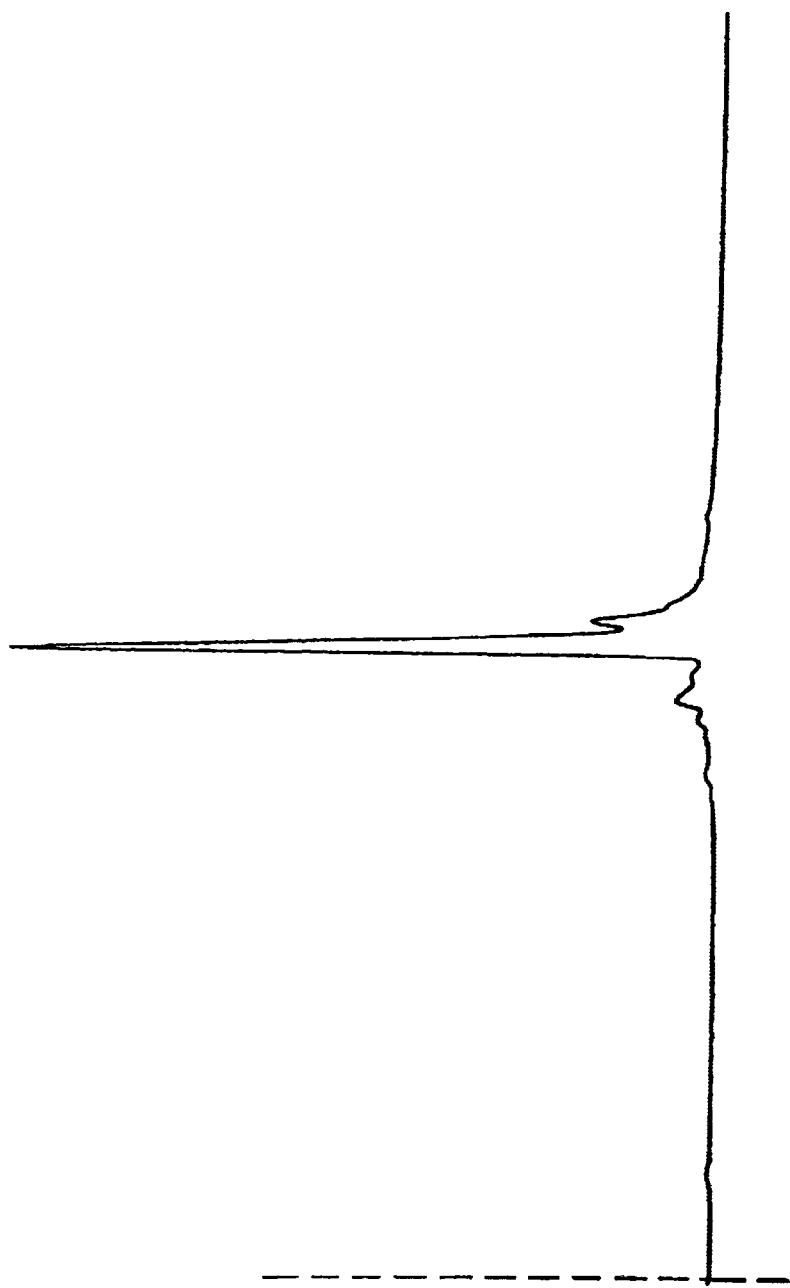

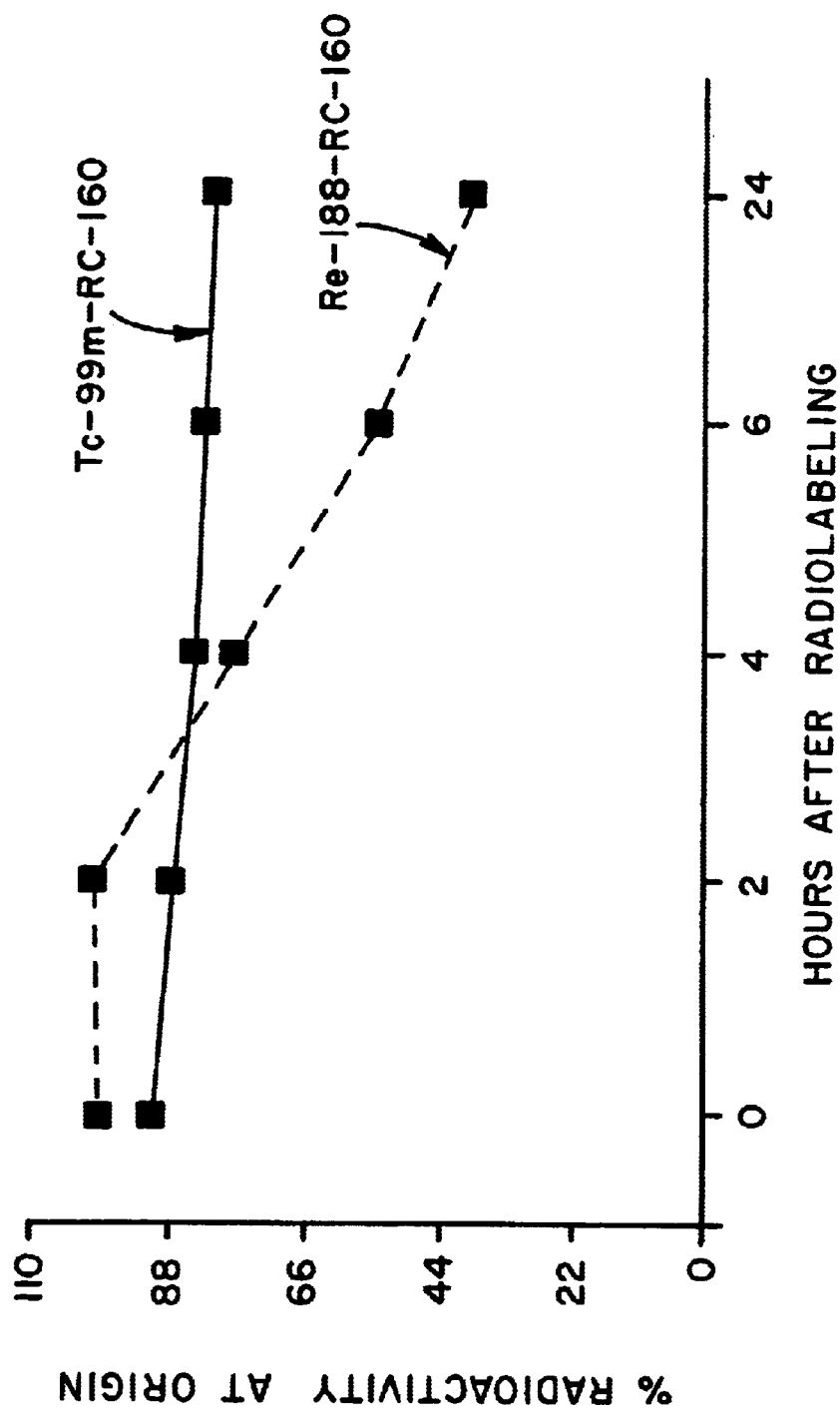

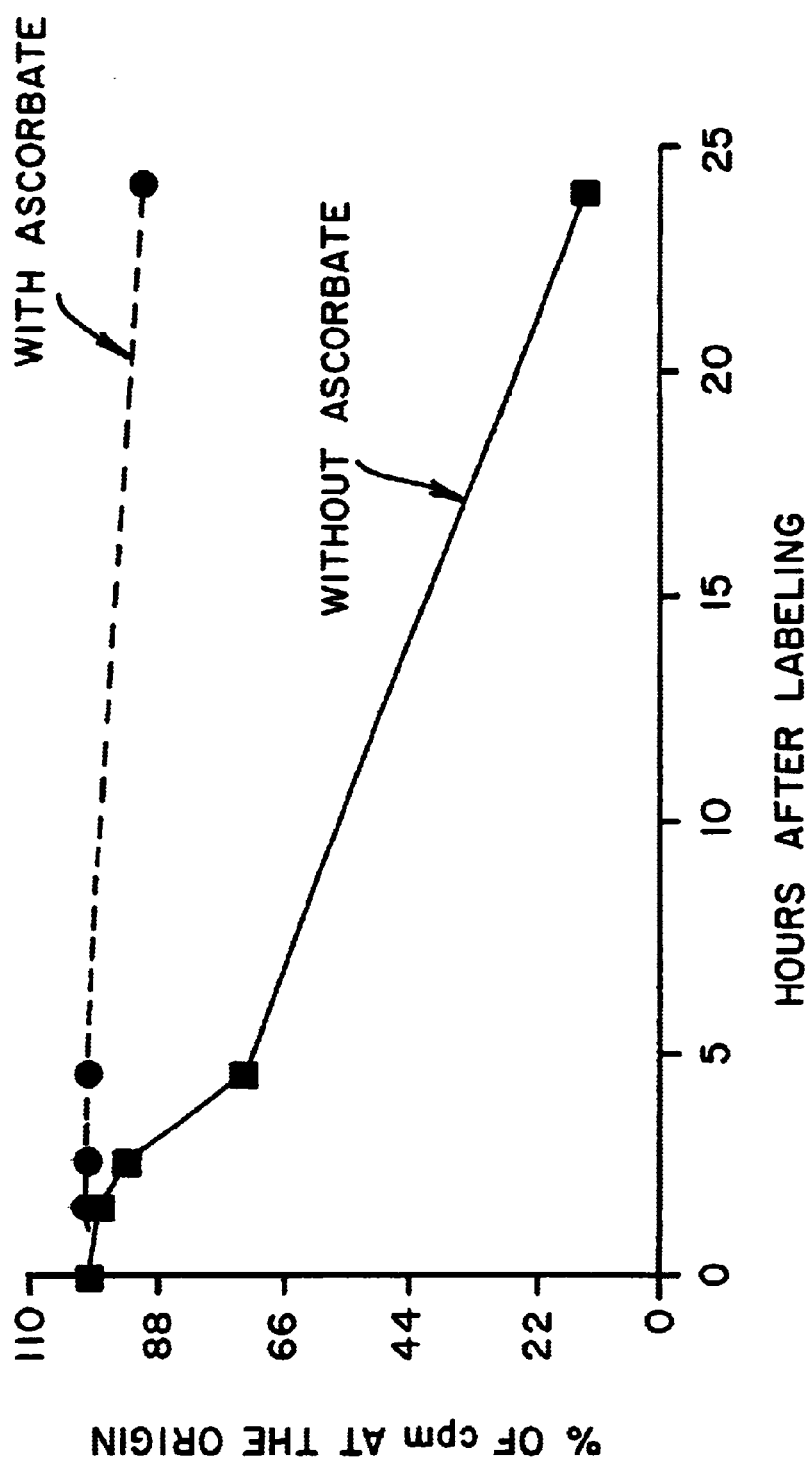

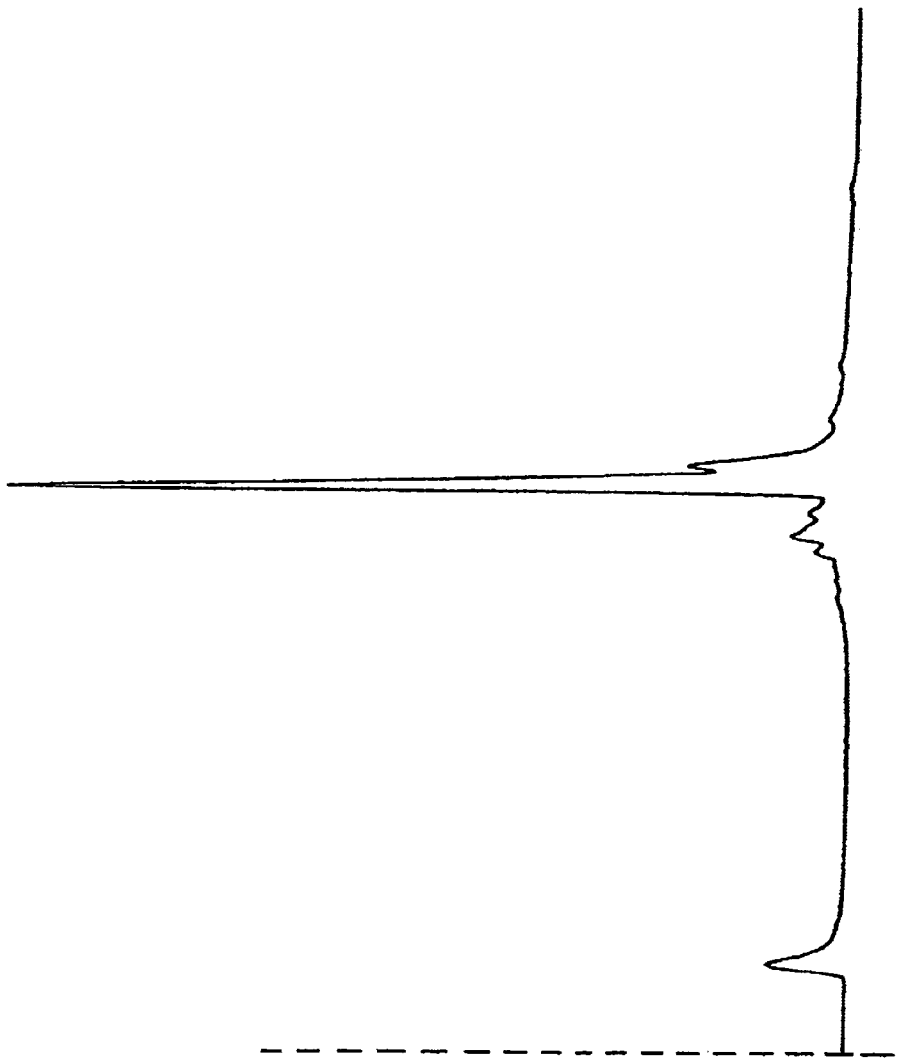

FIG. 9A

| Test Date | ID | HPLC Pk Bound | ITLC %Free | ITLC %Colloid | Cell Binding Assay HL60 | Cell Binding Assay 293 | Cell Binding Assay No Cells | conc during labeling |
|---|---|---|---|---|---|---|---|---|
| 5/15/95 | Froz -11.7mCi | 90.91 | 5.75 | 0.00 | 70.21 | 10.41 | 4.95 | 0.71mg/ml |
| | Lyop -13.2mCi | 80.00 | 2.82 | 0.00 | 77.03 | 7.51 | 1.89 | 1mg/ml |
| 5/30/95 | Lyop -4.97mCi | 87.70 | 3.02 | 0.00 | — | — | — | 1mg/ml |
| | Lyop -16.6mCi | 77.35 | 9.81 | 0.00 | 73.10 | 13.26 | 4.44 | 1mg/ml |
| 6/27/95 | Lyop -20.9mCi | 77.37 | 0.00 | 3.58 | 70.82 | 7.52 | 5.26 | 1mg/ml |
| 7/19/95 | Lyop -19.3mCi | 78.48 | 0.00 | 0.00 | 70.54 81.18(NEW) | 14.28 | 10.62 | 1mg/ml |
| 8/4/95 | RhoMed -15.45mCi | 84.11 | 6.15 | 0.00 | 78.04 | 15.95 | 7.36 | 1mg/ml |
| | UCLA -16.58mCi | 84.08 | 5.46 | 0.00 | 81.65 | 12.59 | 5.54 | 1mg/ml |

LEUKO-1, Lot# LEU50511-1MM-12μg SnT

FIG. 9B

| | | | | | | |
|---|---|---|---|---|---|---|
| 8/21/95 | t=30 min −19.00mCi | 83.56 | 0.00 9.68%** | 3.16 | 74.28 | 17.08 | 8.50 | 1mg/ml |
| | t=2.5 hrs −19.00mCi | 86.70 | 0.00 3.20%** | 4.36 | 77.66 | 11.38 | 4.90 | 1mg/ml |
| 9/7/95 Vial #18 19.5mCi | t=30 min | 90.12 | 0.00 *8.18 | 3.30 *4.48 | 72.63 | 16.14 | 6.56 | 1mg/ml |
| | t=2.5 hrs | 92.81 | 0.00 *10.49 | 7.34 *7.75 | 82.56 | 10.47 | 7.39 | 1mg/ml |
| | t=23 hrs | 86.36 | 3.51 *11.09 | 5.84 *6.87 | 80.13 | 6.10 | 3.45 | 1mg/ml |
| 9/7/95 Vial #19 19.5mCi With Ascorbic Acid | t=30 min NO Ascorb | 92.16 | 0.00 *3.00 | 4.62 *4.30 | 79.54 | 19.78 | 8.60 | 1mg/ml |
| | t=1 hr | 82.87 | 0.00 *5.80 | 7.89 *7.75 | 77.00 | 8.47 | 3.96 | 1mg/ml during labeling |
| | t=2.5 hrs | 89.13 | 0.00 *8.78 | 2.32 *7.15 | 75.29 | 7.77 | 6.41 | 0.25mg/ml after addition of Ascorbic acid |
| | t=24 hrs | 80.23 | 0.00 *14.16 | 11.79 *12.61 | 74.03 | 9.83 | 7.81 | |

*or** Average of strips counted on Gamma Counter and Dose Calibrator

FIG. 10A

| Sample ID | 2hrs post labeling | | | 2hrs post labeling | | 24 hrs post labeling | |
|---|---|---|---|---|---|---|---|
| | HPLC | | ITLC | | ITLC | | |
| | % protein Bound | HPLC Yield | % Free | % Colloid | % Free | % Colloid | |
| Standard SOP | 86.59 | 60.63 | 1.82 | 3.18 | 11.89 | 13.53 |
| w/ascorbic acid during labeling | 73.53 | 37.87 | 3.47 | 2.55 | 17.11 | 8.42 |

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where X is D
<220> FEATURE:
<221> NAME/KEY: MISC_FEATURE
<222> LOCATION: (5)..(5)
<223> OTHER INFORMATION: where X is D
<220> FEATURE:
<221> NAME/KEY: MISC_FEATURE
<222> LOCATION: (11)..(11)
<223> OTHER INFORMATION: where X is NH2

<400> SEQUENCE: 1

Xaa Phe Cys Tyr Xaa Trp Lys Val Cys Trp Xaa
1               5                   10
```

POST-LABELING STABILIZATION OF RADIOLABELED PROTEINS AND PEPTIDES

This is a continuation, of application Ser. No. 09/900,390, filed Jul. 6, 2001, now abandoned was a continuation of Ser. No. 09/393,581, filed Sep. 9, 1999, which issued as U.S. Pat. No. 6,261,536, which was a continuation of application Ser. No. 08/794,311, filed Feb. 3, 1997, which issued as U.S. Pat. No. 6,066,309; which was a continuation-in-part of application Ser. No. 08/794,270, filed Jan. 31, 1997, abandoned, and which claimed priority under 35 U.S.C. §119(e) of U.S. Provisional Application No. 60/011,027, filed Feb. 2, 1996. Each of these prior applications is hereby incorporated herein by reference, in its entirety.

BACKGOUND

1. Field of the Invention

This invention relates to stabilizers for radiopharmaceutical compositions which are added after radiolabeling but prior to administration. Ascorbic acid (and/or a derivative thereof), alone or in combination with other stabilizers, is used to inhibit oxidation loss and autoradiolysis of radiolabeled peptides and proteins.

2. Background Art

A large number of protein-based radiopharmaceuticals are under clinical investigation, and a smaller number have been approved in the United States and other countries. Similarly, peptide-based radiopharmaceuticals are also under clinical investigation, with several approved for clinical use. Therapeutic and diagnostic uses of both protein- and peptide-based radiopharmaceuticals continue to be developed. Typical therapeutic and diagnostic applications are described in U.S. Pat. Nos. 5,078,985; 5,102,990; 5,277,893; 5,443,816; and 5,460,785; and in U.S. patent application Ser. Nos. 08/087,219; 08/269,929 and 08/651,179, incorporated by reference in their entirety.

Protein- or peptide-based radiopharmaceuticals are primarily based upon use of monoclonal antibodies (or fragments thereof) as a targeting vehicle, but other peptides or proteins can also be used, including albumins and hormones. Both intact antibodies (monoclonal and polyclonal) and fragments, made by any method known to the art, as well as peptide mimics of fragments or antibody binding sites can be radiolabeled and used as imaging, diagnostic or therapeutic agents.

A variety of peptide-based radiopharmaceuticals have been investigated, including those in which the peptide is derived from somatostatin. Radiolabeled peptide analogues of somatostatin used for diagnostic imaging include $^{123}$I-labeled Tyr-3-octreotide and $^{111}$In-diethylene tetraamine-pentaacetic acid (DTPA)-octreotide imaging agents. Research is underway on a variety of $^{99m}$Tc-labeled somatostatin analogues, including direct-labeled peptide somatostatin analogues. An $^{111}$In-DTPA-octreotide product is commercially available in the United States and European countries, and is distributed by Mallinckrodt Medical, Inc.

Both protein- and peptide-based radiopharmaceuticals may be radiolabeled by a variety of means. Both peptides and proteins can be directly radioiodinated, through electrophilic substitution at reactive aromatic amino acids. Iodination may also be accomplished via prelabeled reagents, in which the reagent is iodinated and purified, and then linked to the peptide or protein.

The utility of DTPA and EDTA chelates covalently coupled to proteins, polypeptides and peptides is well known in the art. DTPA has been used as a bifunctional chelating agent for radiolabeling a variety of peptides with $^{111}$In, including somatostatin analogues for cancer imaging, α-melanocyte-simulating hormone for imaging melanoma, chemotactic peptides for infection imaging, laminin fragments for targeting tumor-associated laminin receptors and atrial natriuretic peptides for imaging atrial natriuretic receptors in the kidney.

$^{99m}$Tc is a preferred isotope for diagnostic imaging, due to its low cost, ready availability, excellent imaging properties and high specific activities. Two approaches have been described for radiolabeling proteins and peptides with $^{99m}$Tc: direct labeling and bifunctional chelates. Direct labeling methods are generally described in U.S. Pat. Nos. 5,078,985; 5,102,990; 5,277,893; 5,443,816; and 5,460,785 referenced above, in which a variety of methods of direct labeling of peptides and proteins through sulfur-, oxygen- and nitrogen-containing amino acid sequences available for binding are disclosed.

A variety of high affinity chelates to bind $^{99m}$Tc to specific sites on peptides have been developed. In one approach, the bifunctional reagent is first labeled with $^{99m}$Tc, and then conjugated to the peptide. However, multiple species can result, and post-labeling purification is generally required. In another approach, a chelating agent is covalently attached to the peptide prior to radiolabeling. Chelates which have been employed include a variety of N2S2 and N3S ligands, DTPA, 6-hydrazinonicotinate groups, metallothionein and metallothionein fragments.

Isotopes of rhenium, principally $^{186}$Re and $^{188}$Re, have been used to radiolabel proteins and peptides for investigation as therapeutic agents. The chemistry of $^{186}$Re and $^{188}$Re is similar to that of $^{99m}$Tc, though not identical, and both direct and chelate labeling approaches have been used in radiolabeling proteins and peptides with rhenium.

Protein and peptide radiopharmaceutical compositions are known to degrade after radiolabeling, primarily by oxidation losses and by autoradiolysis. Some radiopharmaceuticals, such as $^{99m}$Tc, and especially $^{186}$R and $^{188}$Re labeled compounds, are particularly susceptible to oxidation losses if the isotope is not maintained in a suitable oxidation state. Both technetium and rhenium isotopes normally exist in their highest or +7 oxidation state, which is the stable state, until reduced with stannous or other reducing agents. A technetium or rhenium radiolabeled compound can become unstable if the complexed reduced isotope is oxidized to a higher oxidation state, releasing the bound isotope as free or unbound pertechnetate +7 or free perrhenate +7.

The term "autoradiolysis" includes chemical decomposition of a radiolabeled peptide or protein by the action of radiation emitted from the radioisotope coupled to the peptide or protein. Autoradiolysis may be caused by the formation of free radicals in the water or other medium due to the effect of radiation emitted from the radioisotope. Free radicals are molecules or atoms containing a single unpaired electron, which exhibit high chemical reactivity. Autoradiolysis is a significant problem with high energy β-emitting isotopes, such as rhenium isotopes, and with α-emitting isotopes, but is typically somewhat less of a problem with γ-emitting isotopes, such as $^{99m}$Tc.

A variety of methods have been employed to stabilize radiopharmaceuticals in general, including addition of HSA (human serum albumin) to a composition or keeping it frozen between preparation and use. However, these methods are not reliably effective or practical for use with many radiolabeled peptides and proteins. Substances such as ascorbic acid and gentisic acid have also been used to inhibit the oxidation of the radioisotope, and to limit autoradiolysis by acting as "free radical scavengers" which donate reactive hydrogen atoms to the free radical intermediates yielding a non-reactive molecule. Use of gentisic acid and its derivatives to stabilize radiolabeled proteins and peptides is described in U.S. Pat. No. 5,384,113, incorporated herein by reference, and use of ascorbic acid to stabilize some chemical-based radiolabeled compounds, but not protein- or peptide-based radiolabeled compounds, is described in Tofe, A. J. and Francis, M. D., *J. Nucl. Med.*, 17, 820–825 (1976). However, ascorbic acid has been recognized in the art as unsuitable for use as a stabilizing agent with many chemical-based radiolabeled compounds, presumably because it competes for the $^{99m}$Tc and forms a $^{99m}$Tc-ascorbate complex. Ballinger, J., Der, M., and Bowen, B., *Eur. J. Nucl. Med.*, 6, 154–154 (1981). In fact, because of the stability of Tc-ascorbate complex, ascorbic acid has been labeled with technetium by numerous investigators for use as a potential renal imaging agent. In addition, use of ascorbic acid prior to and during radiolabeling has been described in U.S. Pat. No. 5,011,676, and has been described in *Radiopharmaceuticals*, G. Subramanian, B. A. Rhodes, J. F. Cooper and V. J. Sodd, eds, Society of Nuclear Medicine, New York, 1975, pp. 37–38, as an agent, used either singly or in combination with Fe(III), in technetium labeling of HSA. Despite the promise shown by a number of newly-developed proteins and peptides for diagnostic and therapeutic applications, susceptibility to oxidation loss, autoradiolysis and other impurities may limit use. Therefore, the development of means for the effective stabilization of radiolabeled compounds, without loss due to the stabilizing agent, is a significant and much-needed advancement in the art.

SUMMARY OF THE INVENTION

Accordingly, it is an object of the present invention to provide a composition containing a radiolabeled protein or peptide having improved stability (e.g., against oxidation, autoradiolysis and more generally degradation). Another object is to provide novel methods for stabilizing a radiolabeled protein peptide or polypeptide.

It is a further object of the invention to provide a diluent and a bodying agent, providing volume to the radiolabeled protein or peptide preparation which is helpful in a pharmaceutical or clinical setting for ease of manipulation and administration. It is a further object of the invention to provide a stabilizing agent which further stabilizes a radiolabeled protein or peptide preparation containing excess stannous or stannic ions, preventing formation of Sn-colloids or other radiochemical impurities. It is a further object of the invention to provide a radiolabeled protein or peptide composition which uses a relatively non-toxic and readily obtainable stabilizing agent. It is a further object of the invention to provide stabilized radiopharmaceutical products made by the various methods disclosed hereinabove.

Other objects, advantages, and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combination particularly pointed out in the appended claims.

The present invention provides a method for stabilizing radiopharmaceutical compositions, including compositions based on peptides and proteins, including antibodies. The method comprises adding ascorbate or other stabilizing agents to the pre-radiolabeled composition in an amount effective to prevent degradation of the radiolabeled substance, such as that caused by autoradiolysis of the labeled composition and oxidation loss of the radiolabel.

There is also provided a method of preparing a stabilized peptide or protein radiopharmaceutical composition, comprising the ordered steps of labeling a peptide or protein with a radioisotope to form a radiolabeled pharmaceutical product, said radiolabeled pharmaceutical product being substantially free of any stabilizing agents, and then adding a stabilizing agent consisting of ascorbic acid, or one or more derivatives thereof (such as salts, esters, and mixtures thereof) to the radiolabeled pharmaceutical product. In one embodiment, the radioisotope may be an isotope of rhenium or technetium, and particularly $^{99m}$Tc, $^{186}$Re or $^{188}$Re.

There is also provided a method of preparing a stabilized rhenium-labeled peptide-based somatostatin analogue radiopharmaceutical composition, comprising the ordered steps of labeling said peptide with an isotope of rhenium to form a radiolabeled pharmaceutical product, said radiolabeled pharmaceutical product being heretofore substantially free of any stabilizing agents, and then adding a stabilizing agent consisting of ascorbic acid, its salts, esters, derivatives and mixtures thereof to the radiolabeled pharmaceutical product. In one embodiment, the radioisotope may be $^{186}$Re or $^{188}$Re.

There is also provided a method of preparing a stabilized technetium-labeled anti-SSEA-1 IgM antibody-based radiopharmaceutical composition, comprising the ordered steps of labeling said anti-SSEA-1 antibody with an isotope of technetium to form a radiolabeled pharmaceutical product, said radiolabeled pharmaceutical product being heretofore substantially free of any stabilizing agents, and then adding a stabilizing agent consisting of ascorbic acid, its salts, esters, derivatives and mixtures thereof to the radiolabeled pharmaceutical product. In one embodiment, the radioisotope may be $^{99m}$Tc.

Additionally, the present invention provides stabilized compositions containing a radiolabeled protein or peptide, which compositions have been stabilized by the addition of a stabilizing agent containing ascorbic acid or a derivative thereof to a composition containing said protein or peptide already radiolabeled.

BRIEF DESCRIPTION OF THE FIGURES

FIG. 1A is an elution profile of Re-188-RC-160-labeled with 65 mCi of Re-188 at 6 hours post-labeling from a $C_{18}$-reverse-phase HPLC column. The y-axis in arbitrary units.

FIG. 5. Comparison of Tc-99m- or Re-188-labeled RC-160 over time as analyzed by TLC. Saline was used as a mobile phase. Similar amounts (20 mCi) of each radionuclide were used, and the same formulation (optimized for Re-labeling) was used in the comparison. No post-labeling stabilizer was used.

FIG. 6. Comparative TLC of Re-188-RC-160 with and without post-labeling stabilization with ascorbate.

FIG. 7. Elution profile of Re-188-RC-160 labeled with 65 mCi of Re-188 at 30 hours post-labeling from a $C_{18}$-reverse-phase HPLC column. The γ-axis in arbitrary units.

FIGS. 9A and 9B Labeling of a RhoMed radiopharmaceutical product known as LeuTec-MTM, a $^{99m}$Tc-labeled anti-SSEA-I antibody. (This product is referred to as "Leuko-I" in FIG. 9, which is a summary of the test results from a lot of LeuTecMTM manufactured by RhoMed.) This data shows the difference in radiolabeling yields between unstabilized and stabilized (with ascorbate) product.

FIGS. 10A, 10B and 10C HPLC profile on $^{99m}$Tc-labeled IgM samples showing the difference in yield over time with labeling occurring in the presence of ascorbate or with postlabeling addition of ascorbate.

DETAILED DESCRIPTION

Figure 1B:
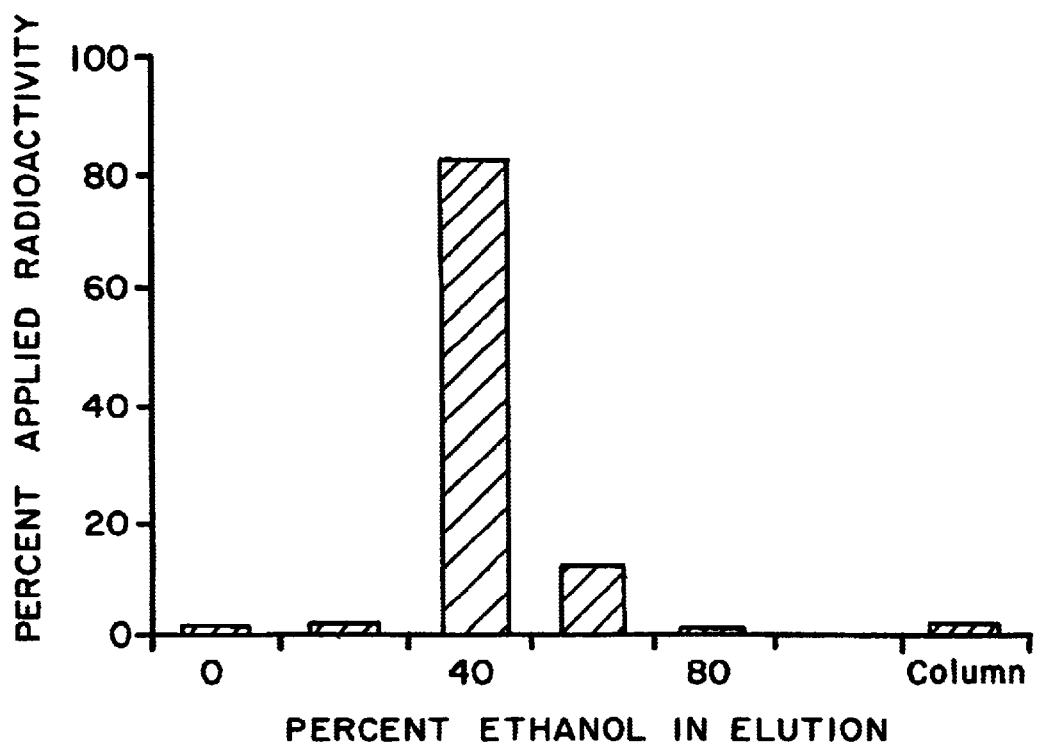
FIG. 1B is an elution profile of Re-188-RC-160 from a $C_{18}$-SepPak column using a step-gradient of acidified ethanol.

The present invention is directed to radiolabeled protein- or peptide-containing compositions with a stabilizing agent added subsequent to radiolabeling but prior to use to prevent oxidation and autoradiolysis. One class of stabilizing agent which is effective at preventing oxidation and autoradiolysis is ascorbic acid (and derivatives thereof). With many protein- and peptide-based radiolabeled compositions, ascorbic acid and its derivatives interfere with radiolabeling if included in the composition prior to or during radiolabeling. However, the inventors have found that, unexpectedly, when added subsequent to radiolabeling (and subsequent to any incubation period), ascorbic acid and its derivatives result in a radiolabeled substance of superior stability and body (volume). The radiolabeled proteins and peptides which are effectively stabilized according to the present invention include radiopharmaceutical drugs having diagnostic or therapeutic applications.

While the methods of this invention are particularly applicable to stabilizing compositions including isotopes of technetium and rhenium, such as $^{99m}$Tc, $^{186}$Re and $^{188}$Re, because of the particular susceptibility of such isotopes to oxidation and/or autoradiolysis, the methods of this invention can be used with compositions including a wide variety of isotopes, including those found in the group consisting of elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Ti, Pb, Bi, Po, At) of the Periodic Table of Elements. Radioisotopes with diagnostic or therapeutic applications include 62Cu, 64Cu, 67Cu, 97Ru, 105Rh, 109Pd, $^{186}$Re, $^{188}$Re, 198Au, 199Au, 203Pb, 211Pb and 212Bi.

The radiolabeled peptide compositions stabilized by means of this invention include proteins, peptides and polypeptides which are naturally-occurring, as well as those produced by chemical synthesis, by recombinant DNA technology, by biochemical or enzymatic fragmentation of larger molecules, or by any other means for producing them. For example, peptides stabilized by the present method include peptide fragments, polypeptides and other structures derived therefrom, generally consisting of a sequence of amino acids. Representative examples of peptides include those derived from laminin, fibronectin, cytokines, lymphokines, serum albumin, fibrinogen, enzymes, hormones, somatostatin, urokinase, tissue plasminogen activator, and protease inhibitors. Peptides will generally comprise fewer than 100 amino acids, and preferably fewer than 60 amino acids, and most preferably comprise between about 4 and about 20 amino acids. The amino acids forming all or a part of the peptide may be naturally occurring amino acids, isomers and modifications of such amino acids, non-protein amino acids, post-translationally modified amino acids, enzymatically synthesized amino acids, isosteric amino acid analogues and the like, so that the term "peptide" includes pseudopeptides and peptidomimetics. The term "peptide" also includes cyclic peptides, bridged peptides (e.g., disulfide-bridged peptides), dimers or multimers of peptides. Radiolabeled protein compositions stabilized by means of this invention include such proteins, whether natural or synthetic, as human serum albumin, fibrinogen, urokinase, gamma globulin, laminin, fibronectin, cytokines, lymphokines, enzymes, enzyme inhibitors, hormones, glycoproteins, and immunoglobulins. The term "protein" as used throughout the specification and claims is intended to include all of the foregoing substances. The protein is typically of mammalian origin, but also includes proteins of plant origin and proteins from prokaryotic cells. Methods of attaching or complexing proteins to other molecules, such as lipids and carbohydrates, including liposomes, are known to those skilled in the art.

Immunoglobulins, a type of protein, include antibodies and antibody fragments (including fragments consisting essentially of an antigenic determinant or antigen binding site), of any species, and include both polyclonal and monoclonal antibodies made by any means, as well as chimeric and genetically engineered antibodies, hybrids, and fragments of all of the foregoing. This includes immunoglobulins of any class, such as IgG, IgM, IgA, IgD or IgE, of any species origin, including human beings, chimeric antibodies or hybrid antibodies with dual or multiple antigen or epitope specificities, and fragments of all of the foregoing, including F(ab)2, F(ab)2, Fab, Fab and other fragments, including hybrid fragments, and further includes any immunoglobulin or any natural, synthetic or genetically engineered protein that functionally acts like an antibody by binding specifically to a given antigen to form a complex, including single chain antibodies. The terms "antibody" or "antibodies" as used throughout the specification and claims are intended to include all such antibodies and antibody fragments.

The products stabilized by means of the invention set forth herein can be used for both medical applications and veterinary applications. Typically, the product is used in humans, but may also be used in other mammals. The term "patient" is intended to include a mammal, and is so used throughout the specification and in the claims. The primary applications of the invention involve human patients, but the invention may be applied to laboratory, farm, zoo, wildlife, pet or sport animals.

The products stabilized by means of the invention set forth herein can be used as imaging agents, for example, to view tissues in order to monitor normal or abnormal metabolic events, to localize normal or abnormal tissues, to localize diseases, to diagnose or treat diseases, and to bind to blood constituents, including blood cells, such as lymphocytes, for subsequent localization of diseases, infections, and abnormal tissues. The application and medical use of the product depends on the type of protein or peptide and the type of radioisotope used.

The protein or peptide is first labeled with a radioisotope which can be accomplished using known techniques, and once labeling is complete, it is then stabilized according to the invention. The radioisotope may generate gamma rays, beta particles, or positrons which are converted into gamma rays upon collision with electrons. The radioisotope may be used in diagnostic imaging procedures including gamma scintigraphy, specific photon emission computerized tomography, or positron emission tomography, -or may be used therapeutically.

With $^{99m}$Tc, $^{186}$Re or $^{188}$Re labeled peptides or proteins, regardless of the particular method of radiolabeling employed, the addition of ascorbic acid to achieve concentrations between about 0.001 wt % and 5 wt % to the composition post-labeling increases the stability of the radiolabeled composition, with apparent increased resistance to oxidation and/or radiolytic decomposition. If excess stannous or stannic ions are present in the composition of the labeled peptide or protein, the addition of ascorbic acid also prevents formation of Sn-colloids and other radiochemical impurities. This thus allows sufficient stannous ion to be added to a preparation to be radiolabeled to insure complete reduction of the pertechnetate or perrhenate, even if there is some oxidation loss of stannous to stannic ion, without formation of undesirable radiochemical impurities frequently found with excess tin. As stated above, presence of ascorbic acid or a derivative thereof in a composition containing peptides and proteins, and radiolabeling agents before the completion of radiolabeling, regardless of the method of radiolabeling, inclusion of ascorbic acid prior to ordinary labeling has a detrimental effect on radiolabeling yields. When derivatives are used an equivalent amount (on a molar basis) can be used.

Addition of ascorbic acid or a derivative thereof post-labeling to the compositions (in which ascorbic acid has been present prior to completion of radiolabeling) does not cure the problem created by the presence of ascorbic acid prior to or during labeling. The present invention thus requires that the stabilizing agent (ascorbic acid or a derivative thereof) be added to the composition containing a radiolabeled peptide or protein only after radiolabeling is complete (i.e., after the label has been attached to the peptide or protein and any incubation period has elapsed). The requirement that the ascorbic acid or other stabilizing agent be added after the protein or peptide is labeled with the radioisotope is critical, in that adding ascorbic acid or another stabilizing agent prior to or during radiolabeling can adversely affect the radiochemical purity and yield of the radiolabeled preparation. Such post-labeling stabilization yields a superior result. That addition of ascorbic acid and other stabilizing agents post-labeling would produce superior radiochemical yields was new and surprising.

One particularly beneficial application of the instant invention is that antioxidants, notably ascorbic acid (and derivatives thereof), inhibit radiolysis and free radical damage to proteins or peptides labeled with isotopes emitting high energy photons or particles, such as the 2 MeV beta particle emitted upon decay of $^{188}$Re. Free radical degradation in particular can be significant, and generally increases with both time and increased amounts of radioactivity in the preparation.

The use of ascorbic acid or derivative has the added advantage in a pharmaceutical or clinical setting for the purpose of "bulking" the preparation, that is, giving the preparation a certain required minimum volume for easy manipulation and use. In addition, preparations of ascorbic acid (or derivative) for injection are commercially available, and exhibit little or no toxicity. If not available, they can be synthesized using known techniques.

A protein or peptide radiolabeling kit may be employed, which will contain one or more vials containing the protein or peptide to be radiolabeled, and may contain a transfer ligand, a reducing agent, depending on the radioisotope to be employed, other radiolabeling reagents and one or more excipients. The contents of a vial may be lyophilized, frozen or in liquid formulation. The radioisotope, typically in an aqueous solution, is added to the vial containing the protein or peptide to be radiolabeled to initiate radiolabeling. It is key that the radiolabeling vial not include ascorbic acid or derivative since their presence may adversely affect radiolabeling. Rather, ascorbic acid and other stabilizing agents are conventionally included in the radiolabeling kit in a separate vial, or may be obtained from other sources in a separate vial. Depending on the method of radiolabeling employed, after addition of the radioisotope to the radiolabeling vial and mixing as required to solubilize the components, the radiolabeling vial is allowed to incubate for a period of time, generally ranging from 15 minutes to one hour, at a temperature ranging from room temperature to 100° C. After the incubation period is completed, unreacted label and/or excess reducing agent are optionally removed, the ascorbic acid or derivative thereof then added to the radiolabeled protein or peptide in the radiolabeling vial. The amount and molar concentration of ascorbic acid added will depend on the formulation, the desired dose volume, the type of radioisotope, and the quantity of radiation. Commercially available compositions containing ascorbic acid (or a derivative) may be used, typically containing 500 mg/2 ml ascorbic acid, with the volume added ranging from 10 $\mu$l to 2 ml, and preferably from 250 $\mu$l to 1 ml. The derivative may be a physiologically acceptable water soluble salt of ascorbic acid, such as sodium ascorbate, potassium ascorbate, lithium ascorbate, etc. or ester of ascorbic acid. When a derivative of ascorbic acid is employed, an equivalent amount (on a molar basis) is used.

Once the stabilizing agent is added to the radiolabeled protein or peptide, the composition may be prepared for administration. Typically, the radiolabeled composition is administered parenterally, and most commonly intravenously, but other forms of administration are contemplated and possible.

Preferably, the stabilizer of the invention is added as soon as radiolabeling is complete. If any purification of the radiolabeled protein is necessary, the stabilizer can be added after such purification. It is an advantage of the invention, however, that incorporation of the stabilizer in compositions containing excess stannous ion prevents formation of quantities of stannous colloids and other radiochemical impurities that would interfere with performance of the radiolabeled protein or peptide for its intended imaging diagnostic or therapeutic purpose.

The invention is further illustrated by the following non-limiting examples.

EXAMPLE 1

Preparation of a Stabilized Rhenium-Labeled Rc-160 Peptide-Based Radiopharmaceutical Composition RC-160 is a cyclic somatostatin analogue with the general structure:

D-Phe-Cys-Tyr-D-Trp-Lys-Val-Cys-Trp-NH$_2$(SEQ. ID NO. 1)

Figure 2A:
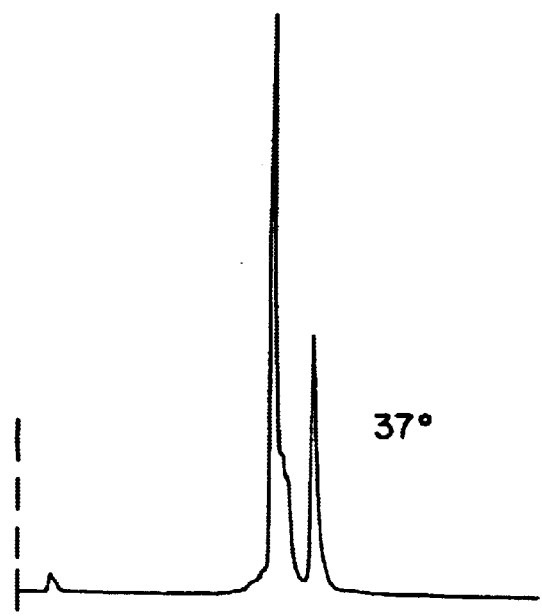
FIGS. 2A and 2B Comparative elutions profiles of Re-188-RC-160 radiolabeled at either 90° C. or 37° C.
Figure 2B:
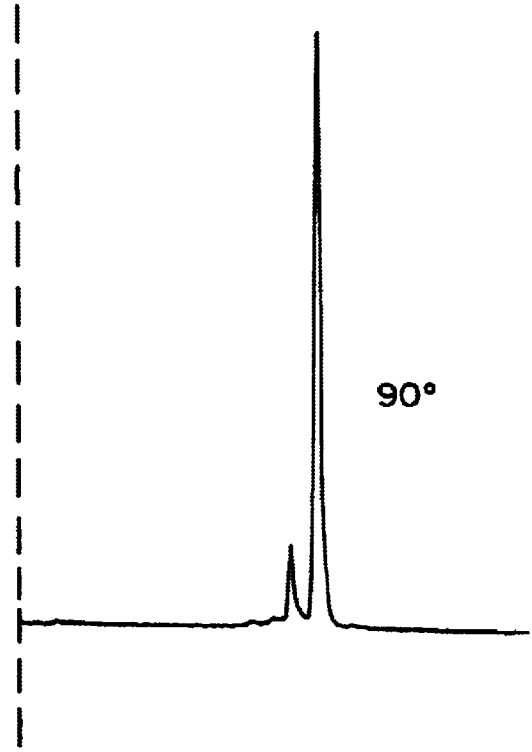
Figure 3:
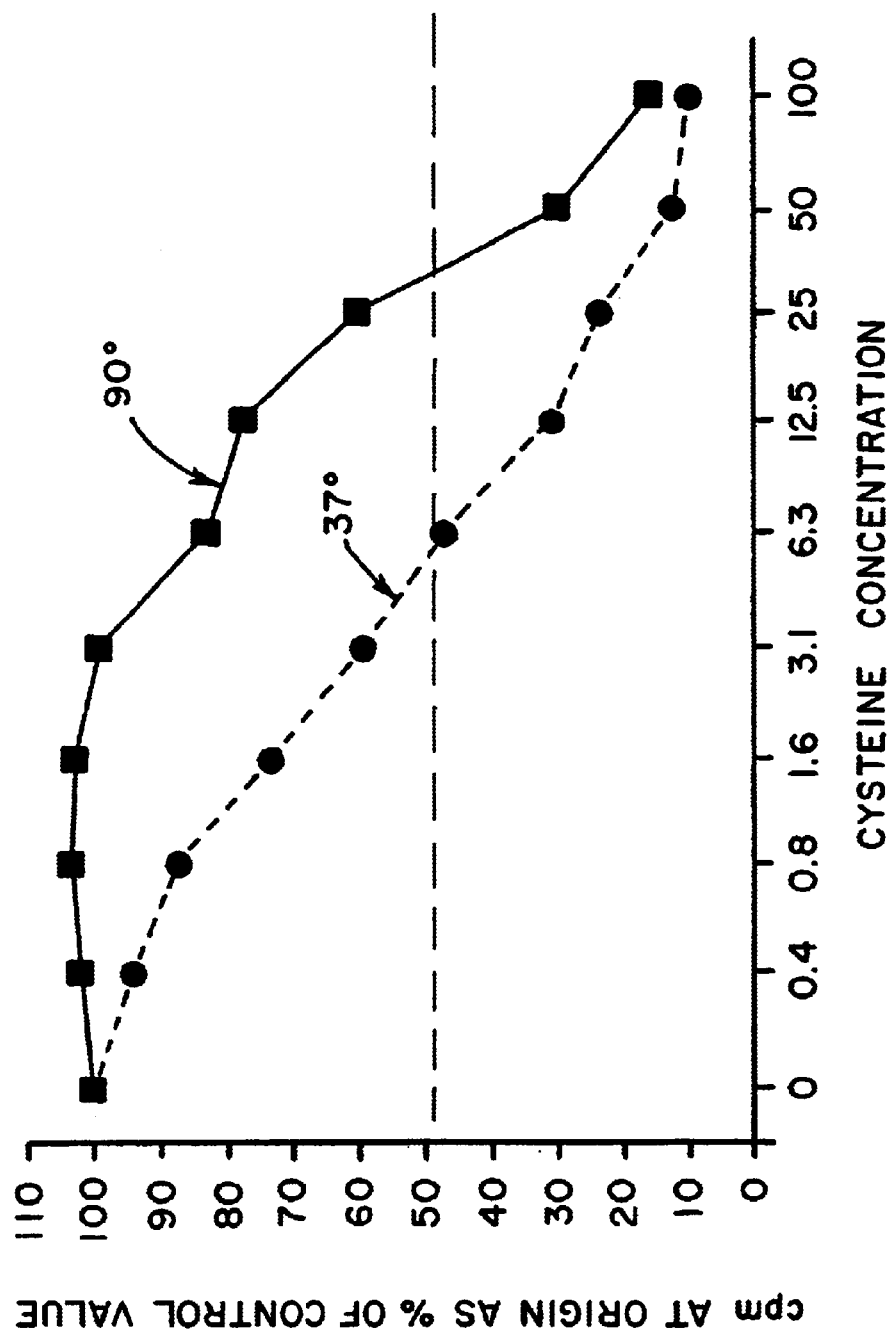
FIG. 3. Displacement of Re-188 from Re-188-RC-160 using increasing concentrations of cysteine as a challenge agent.
Figure 4:
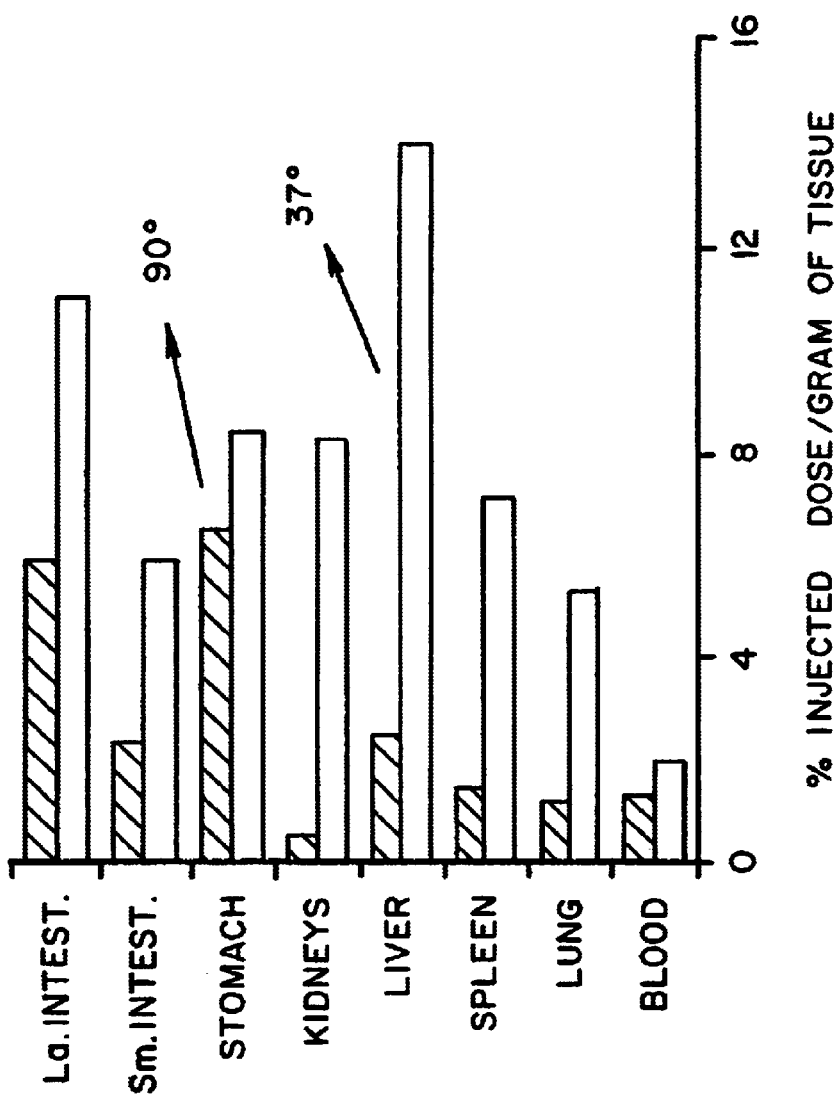
FIG. 4. Comparative biodistribution of Re-188-RC-160 radiolabeled at either 90° C. or 37° C. in normal female mice.
Figures 8A, 8B:
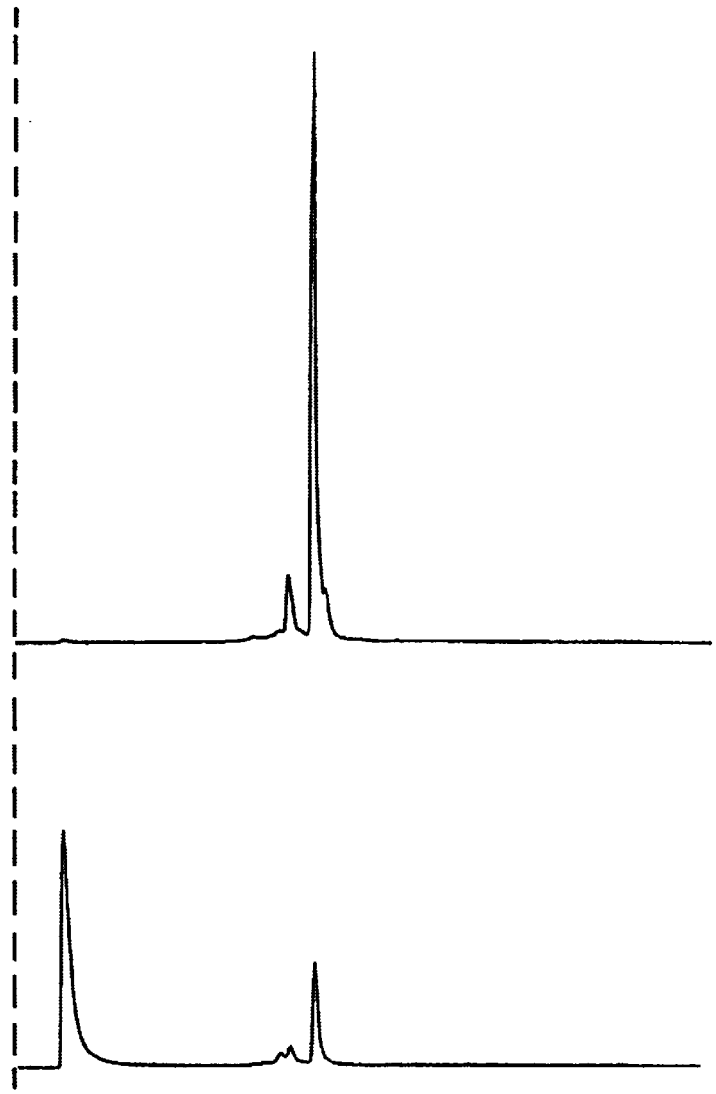
FIGS. 8A and 8B Comparative elution profiles of Re-188-RC-160 with ascorbate added after the radiolabeling (top) or before the radiolabeling (bottom). Both preparations were radiolabeled with 10 mCi (370 Mbq) of Re-188.

Radiolabeling kits were prepared using aseptic techniques, with each kit prepared in a 10 ml serum vial using a 2 ml liquid fill. The liquid fill contained 200 µg of RC-160 peptide in 45 mM sodium potassium tartrate, 10 mM potassium hydrogen phthalate buffer, pH 5.0, in 5 mM stannous tartrate with 1% maltose added as a freeze-drying excipient. Each kit contained a maximum of 1.19 µg of tin. After filling, the vials were lyophilized, the head space gas filled with nitrogen, and the vials stoppered and crimped. Lyophilized vials were then stored refrigerated at 2–80C. To label a kit, 4–5 ml of 188Re-perrhenate solution containing 10–100 mCi was added to the kits, and the kits then heated in a boiling water bath for 30–45 minutes. Following a brief cooling period, 2 ml of ascorbic acid for Injection, U.S.P., was added to the labeled kit through a 0.22 micron filter. Two types of parenteral ascorbate were used with similar results, Ascorbic Acid for Injection, U.S.P., 500 mg/2 ml, and Ascorvit™ (a preparation of ascorbate) 100 mg (Jenapharm, Germany). An elution profile from an analytical HPLC at 6-hours post-labeling is shown in FIG. 1A. In this study, RC-160 was radiolabeled at pH 5.0 for 30 minutes at 90° C. and ascorbate was added postlabeling. The temperature effect is shown in FIGS. 2A and 2B: 19 minutes for 37° C. and 21 minutes for 900C. Also shown in FIG. 1B is an elution profile of Re-188-RC 160 from a C18 column using a step-gradient of acidified ethenol. The results are consistent with the HPLC. $^{188}$Re-RC-160 to which ascorbate was not added was found to be stable for only up to two hours post-labeling; however, after that the $^{188}$Re began to uncouple from the peptide as determined by TLC (using silica-coated thin layer chromatography strips) and confirmed by RP-HPLC (analytical reverse phase HPLO using a C18 column eluted with a continuous gradient of acetonitrile and analyzed by a post-column radioisotope detector, generally at a flow rate of 1 ml/minute). This uncoupling occurred with 188Re, but not with Tc-$^{99m}$ when used in the same amounts, 20 mCi, suggesting the effect was specific to rhenium at this particular concentration. Post-labeling addition of ascorbate was found to essentially eliminate the uncoupling and stabilize the 188Re-RC-160. FIG. 6. An HPLC profile at 30 hours post-labeling with 65 mCi of $^{188}$Re to which ascorbate was added after labeling demonstrated that very little free rhenium could be found. FIG. 7 and FIGS. 1A and 1B. Cysteine displacement studies demonstrated that the Re-peptide bond strength was not altered by addition of the ascorbate post-labeling. Briefly, aliquots of 100 µl cysteine dissolved in phosphate buffer saline (pH 7.4 with 1 M NaOH) were diluted in separate microfuge tubes to result in a doubling dilution. 100 µl of Re188-RC-160 was added to each tube and mixed by inversion. The samples were incubated at 45 minutes at 37° C. or 90° C. A 10 µl aliquot of each sample was then spotted on heat-treated ITLC strip and chromatographed in PBS, pH 7.4 until the solvent was 0.5 cm from the strip top. The amount of displacement was expressed as % of total radioactivity at the solvent front. The results for two experiments conducted respectively at 37° and 90° C. are shown at FIG. 3. In a related manner, comparative biodistribution profiles of Re-188-RC-160 at 2 hours post injection into the tail vein of adult, female BALB/c mice (≈25 g weight) (n≧5/group) with each animal receiving 0.2 ml containing approximately 4 µCi. Selected organs as shown in FIG. 4 were resected and weighed and the associated radioactivity was determined as a percentage of injected dose pr gram of tissue. The percent dose from blood, bone and muscle was calculated assuming 7, 8.2 and 40% of total body weight for these tissues. 37° C. and 90° C. were the two temperatures at which radio labeling was performed.

Addition of the well known general purpose stabilizer/preservative sodium sulfite (1 mg/ml pH 7.4), sodium bisulfite (1 mg/ml, pH 5.5), or mixtures of ascorbate and sodium sulfite (Ascorvit™ formulation), sodium bisulfite, or EDTA (Ascorbate for Injection, U.S.P., formulation) were also effective in stabilizing the $^{188}$Re-RC-160, although not as effective as using ascorbate alone. The addition of 50 mg/m 1 ascorbate yielded the same results as adding 250 mg/ml of ascorbate.

Addition of ascorbate after radiolabeling was found to result in stabilization. When the same amount and concentration of ascorbate was added prior to the addition of the rhenium, the RC-160 was not effectively radiolabeled. The results obtained by analytical RP-HPLC were confirmed by TLC studies and by isocratic elutions from C-18 SepPak columns. Even when the amount of ascorbic acid added prior to the addition of the rhenium was reduced to 400 µg, the radiolabeling was severely compromised. A side-by-side comparison of the results obtained by RP-HPLC revealed an elution profile indicative of inefficient radiolabeling in the presence of this low amount of ascorbic acid. The RP-HPLC results were confirmed by TLC. In the case of the preparation radiolabeled in the presence of 400 µg of ascorbic acid, further post-addition of addition of ascorbic acid after the labeling did not result in any improvement in the labeling efficiency. The addition of ascorbate, or ascorbate/sulfite solutions, maximized the reduction of the peptide RC-160, which is present in excess, without compromising $^{188}$Re-RC-160. The radiolabeling kit could be formulated with an excess of stannous ions and RC-160 to accommodate a variety of labeling situations. In the presence of $^{188}$Re, the RC-160 and stannous ions interact to result in what is believed to be metal-cyclized $^{188}$Re-RC-160. The $^{188}$Re-RC-160 was demonstrated by RP-HPLC not to be identical with stannous-ion-reduced RC-160, or RC-160 reduced with dithiothreitol. Since $^{188}$Re is produced essentially carrier-free from a 188W/$^{188}$Re generator, it is hypothesized that excess stannous ions will reduce the RC-160 not complexed to $^{188}$Re. The post-labeling addition of ascorbate therefore aids the reduction of excess RC-160, thereby rendering it essentially biologically inactive and unable to compete effectively with $^{188}$Re-RC-160 in vivo for binding to receptors. The net result is a stable radiolabeled peptide with a very high specific activity.

EXAMPLE 2

Stabilization of a $^{99m}$Tc-Labeled IgM Antibody for Diagnostic Imaging

Two different lots of radiolabeling kits for an IgM antibody, anti-SSEA-1, were prepared, with each kit containing a lyophilized vial containing:

| Ingredient | Weight Per Kit |
| --- | --- |
| Reduced, stannous-protected anti-SSEA-1 murine IgM monoclonal antibody | 250 μg |
| Maltose | 12.5 mg |
| Succinic acid (CH2COOH)2 | 295 μg |
| Potassium sodium tartrate KNaC4H4O6.4H2O | 250 μg |
| Glycine NH2CH2COOH | 28 μg |
| Edetate Disodium C10H14N2O8Na2.2 H2O | 5 μg |
| Stannous tartrate | 27 μg |

Two different radiolabeling methods were employed; in the first method, each vial was radiolabeled by the addition of $^{99m}$Tc sodium pertechnetate in a volume of 1.0 ml saline, followed by incubation for 30 minutes at 37° C. The radiolabeled antibody was then evaluated. In the second method, each vial was radiolabeled by the addition of $^{99m}$Tc sodium pertechnetate in a volume of 0.25 ml saline, incubated for 30 minutes at 37° C., and then 0.75 ml of a 500 mg/2 ml Ascorbic Acid for Injection, U.S.P., solution was added. The radiolabeled antibody to which the ascorbic acid stabilizing agent had been added was then evaluated. The net immunoreactivity was assessed by measuring binding to cells known to express the antigen for which anti-SSEA-1 is specific, measuring binding to cells known not to express the antigen, and subtracting the difference. In all cases, the net immunoreactivity was higher by the second method in which ascorbic acid stabilizing agent had been added. In one lot of kits, the net inmunoreactive fraction was 51% when ascorbic acid stabilizing agent was added, and 46% when it was not added. In another lot of kits, the net immunoreactive fraction was 59% when ascorbic acid stabilizing agent was added, and 42% when it was not added.

EXAMPLE 3

Formulation of a $^{99m}$Tc-Labeled IgM Antibody Radiolabeling Kit for Diagnostic Imaging A radiolabeling kit was formulated which included a 3 ml reaction vial containing the following lyophilized components:

| Component | Content Per Kit |
| --- | --- |
| Modified, stannous-protected anti-SSEA-1 murine IgM monoclonal antibody | 250 μg |
| Maltose | 12.5 mg |
| Succinic acid | 221 μg |
| Potassium sodium tartrate U.S.P./N.F. | 522 μg |
| Glycine U.S.P./N.F. | 28 μg |
| Disodium Edetate Dihydrate U.S.P./N.F. | 9 μg |
| Stannous tartrate | 54 μg |

The formulation pH is adjusted to 6.2±0.1 with NaOH and/or HCl prior to dispensing 0.50 ml per vial and lyophilizing. The product contains no bacteriostatic preservative. Minimum stannous tin is 10 micrograms and total tin is 24 micrograms. One 2 ml ampule of commercially available Ascorbic Acid Inject ion, U.S.P. (Ascorbic Acid 250 mg/ml and Edetate Disodium 0.025% in water for injection) is included in the radiolabeling kit. Ascorbic Acid solution (0.75 ml) is added after $^{99m}$Tc labeling as a stabilizer for the reconstituted product. To radiolabel, the 3 ml reaction vial with lyophilized components is removed from 2–8° C. storage and allowed to come to room temperature. Without the addition of air, the contents of the vial are aseptically reconstituted with up to 40 mCi (1500 MBq) of Sodium Pertechnetate $^{99m}$Tc Injection (0.25 ml) from a fresh generator elution. The vial is gently swirled until the lyophilized product is completely dissolved. The reaction vial containing Sodium Pertechnetate $^{99m}$Tc Injection is incubated for 30 minutes at 37° C. 0.75 ml of Ascorbic Acid Injection, U.S.P. is then added to the reaction vial and gently swirled to mix. In general, increased stability, as a function of time, results when ascorbic acid is added after radiolabeling. If radiolabeling is performed in the presence of ascorbic acid, in general decreased radiolabeling yields and increased radiochemical impurities are observed, with radiochemical impurities including unbound $^{99m}$Tc-sodium pertechnetate and $^{99m}$Tc-labeled colloid. Dilution of the pre-radiolabeled preparation with commonly used clinical diluents such as dextrose 5%, 0.9% saline, or water for injection, rather than an ascorbic acid solution, also resulted in increased radiochemical impurities.

EXAMPLE 4

Effect of Post—Labeling Ascorbic Acid Stabilization on $^{99m}$Tc-Labeled IgM Antibody Preparations Containing Varying Stannous Concentrations Three different anti-SSEA-1 IgM radiolabeling kits were prepared as in Example 3, except that one kit contained a total of 18 g of stannous tartrate, another kit contained a total of 24 g of stannous tartrate, and a third kit contained a total 30 g of stannous tartrate. Each kit was labeled with 20 mCi of $^{99m}$Tc sodium pertechnetate in a volume of 250 μl, with incubation for 30 minutes at 37° C. Following incubation, 50 μl of each radiolabeled preparation was removed, to which was added 150 μl of an ascorbic acid solution. Each of the resulting six different preparations was tested for immunoreactivity as described in Example 2. In each case, the negative cell binding was substantially lower in the preparations containing ascorbic acid. At the highest stannous concentration, negative cell binding was 14.5% in the preparation which did not contain ascorbic acid, and 2.9% in the preparation which did contain ascorbic acid, demonstrating the stabilizing effect of ascorbic acid on high tin preparations.

Figure 10B:
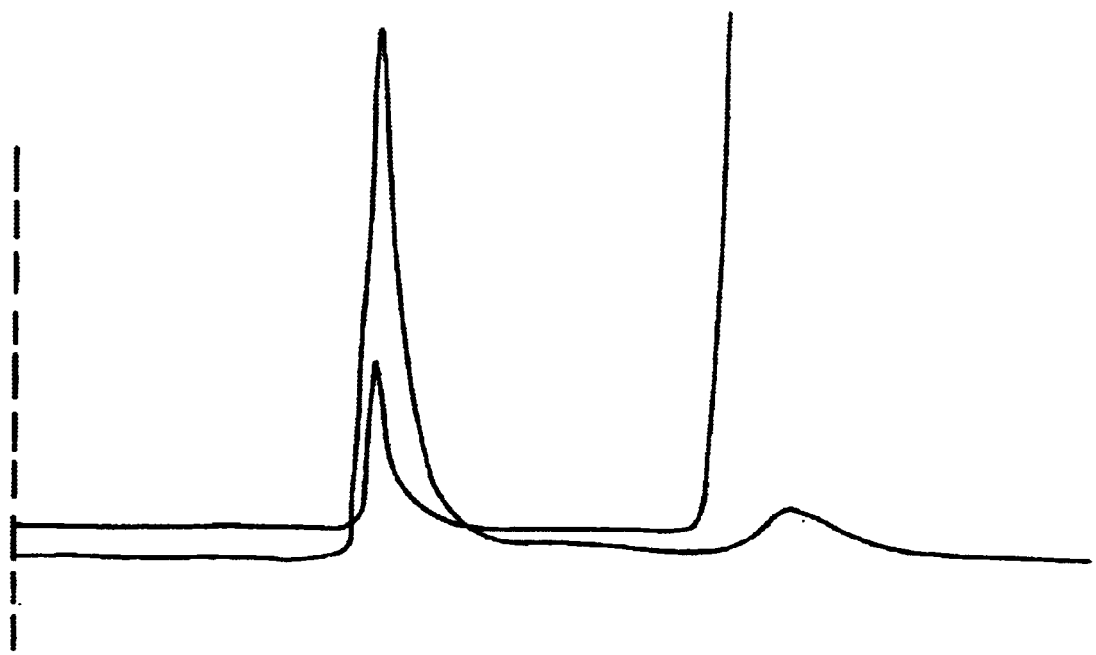
Figure 10C:

The inclusion of ascorbic acid into four different preparations of this IgG antibody, prior to technetium labeling, adversely affects labeling yields, blood levels, and the resistance of the labeled antibody to challenge with cysteine. Ascorbic acid was not added to any of the preparations after labeling, since that was not the intent of these particular experiments. FIGS. 10A–10C show HPLC profiles of $^{99m}$Tc-labeled IgM samples, showing the difference in yield over time with labeling occurring in the presence of ascorbate on the one hand, and addition of ascorbate post-labeling on the other.

EXAMPLE 5

Effect of Ascorbic Acid Added During Radiolabeling of $^{99m}$Tc-Labeled Human Gamma Globulin $^{99m}$Tc-labeling kits were formulated using polyclonal human gamma globulin as the protein to be radiolabeled. A variety of reducing agents, including dithionite, sulfite, and tetrathionate were employed, with stannous used to reduce the $^{99m}$Tc sodium pertechnetate. Each type of different kit was radiolabeled both with and without ascorbic acid in the radiolabeling solution, and in each case the presence of ascorbic acid during radiolabeling adversely affected labeling yields, blood levels obtained upon intravenous injection of the radiolabeled preparation into experimental animals, and the resistance of the labeled antibody to challenge with cysteine.

Data are presented in FIGS. 9A and 9B relating to the labeling of a RhoMed radiopharmaceutical product known as LeuTec-MTM, a $^{99m}$Tc-labeled anti-SSEA-I antibody. (This product is referred to as "Leuko-I" in FIGS. 9A and 9B, which are a summary of the test results from a lot of LeuTecMTM manufactured by RhoMed.) This data shows the difference in radiolabeling yields between unstabilized and stabilized (with ascorbate) product. This data, especially that circled and marked "added post-labeling", shows that the composition tends to remain more stable than those compositions where other diluents were used.

All of the foregoing are merely illustrative, and other equivalent embodiments are possible and contemplated. Although the invention has been described with reference to these preferred embodiments, other embodiments can achieve the same results. Variations and modifications of the present invention will be obvious to those skilled in the art. The appended claims are intended to encompass all such modifications and equivalents. The entire disclosures of all applications, patents, and publications cited above are hereby incorporated by reference.

TABLE 1

Comparative effect of various post-labeling compounds on the elution of Re-188-RC-160 from $C_{18}$ SepPak columns. The top panel illustrates results obtained with ascorbate (50 mg/ml, pH 6.0), sodium sulfite (1 mg/ml, pH 7.4) or sodium bisulfite (1 mg/ml, pH 5.5). The bottom panel illustrates results obtained with Ascorbate for Injection, USP, or the Ascorvit formulation.

| ETHANOL | % OF TOTAL RADIOACTIVITY ASSAYED | | | |
|---|---|---|---|---|
| | SALINE | ASCORBATE | SULFITE | BISULFITE |
| 0–20% | 0.8 | 0.7 | 7.0 | 1.0 |
| 40–60% | 85.4 | 96.4 | 35.8 | 94.0 |
| 80–100% | 4.0 | 0.9 | 3.8 | 1.8 |
| column | 9.7 | 1.8 | 3.5 | 3.3 |

| | SALINE | ASCORBATE FOR INJECTION | ASCORVIT |
|---|---|---|---|
| 0–20% | 0.8 | 0.7 | 1.0 |
| 40–60% | 85.4 | 91.5 | 94.0 |
| 80–100% | 4.0 | 1.3 | 1.8 |
| column | 9.7 | 6.6 | 3.3 |

TABLE 2

Effect of reduced amounts (400 µg) of ascorbic acid on the labeling efficiency of Re-188-RC-160. Ascorbic acid was introduced along with the Re-188, and the results compared to those obtained without the addition of ascorbic acid during the labeling. Both preparations were labeled on the same day using the same batch and amount of Re-188 (20 mCi, 740 MBq).

| | % OF TOTAL RADIOACTIVITY | |
|---|---|---|
| | NO ASCORBATE | PLUS ASCORBATE |
| 10% ethanol | 0.9 | 52.4 |
| 85% ethanol | 97.0 | 46.2 |
| column | 2.1 | 1.4 |

What is claimed is:

1. A method for stabilizing a diagnostic radionuclide composition comprising a protein radiolabeled by direct radiolabeling with $^{99m}$Tc, said method comprising adding a stabilizer selected from the group consisting of ascorbic acid and water soluble salts, esters and mixtures thereof to said composition, wherein said stabilizer is present in an amount sufficient to inhibit oxidation loss and autoradiolysis of said radiolabeled protein, and wherein prior to addition of said stabilizer, said radiolabeled protein is present in a composition which is substantially free of said stabilizer.

2. The method of claim 1 wherein said stabilizer is present in a pharmaceutically acceptable carrier.

3. The method of claim 2 wherein said protein is radiolabeled at a concentration of between 0.5 and 2 mg/ml, and wherein after radiolabeling and upon addition of said stabilizer in said pharmaceutically acceptable carrier said protein is at a concentration of between 0.1 and 0.5 mg/ml.

4. The method of claim 1, wherein said protein is a monoclonal antibody.

5. The method of claim 4, wherein said monoclonal antibody is an immunoglobulin.

6. The method of claim 5, wherein said immunoglobulin is an anti-SSEA-1 murine monoclonal antibody.

* * * * *